US00PP15398P2

(12) United States Plant Patent
Lommerse

(10) Patent No.: US PP15,398 P2
(45) Date of Patent: Dec. 7, 2004

(54) ***SANVITALIA* PLANT NAMED 'QUHA 4015/1'**

(50) Latin Name: *Sanvitalia procumbens*
Varietal Denomination: QuHa 4015/1

(75) Inventor: Henry Lommerse, Mariahout-Laarbeek (NL)

(73) Assignee: Kiept Seeds Holland, Venhuizen (NL)

( * ) Notice: Subject to any disclaimer, the term of this patent is extended or adjusted under 35 U.S.C. 154(b) by 36 days.

(21) Appl. No.: 10/259,939

(22) Filed: Sep. 29, 2002

(51) Int. Cl.[7] ..... A01H 5/00
(52) U.S. Cl. ..... Plt./263

(58) Field of Search ..... Plt./263

(56) References Cited

PUBLICATIONS

Upov–rom hits on 'Yellow Beauty', Feb. 16, 2001.*

* cited by examiner

*Primary Examiner*—Anne Marie Grunberg
(74) *Attorney, Agent, or Firm*—C. A. Whealy

(57) ABSTRACT

A new and distinct cultivar of *Sanvitalia* plant named 'QuHa 4015/1', characterized by its low mounding and spreading plant habit; dark green-colored foliage; early and freely flowering habit; and bright yellow-colored ray florerts.

1 Drawing Sheet

Botanical classification/cultivar designation: *Sanvitalia procumbens* cultivar QuHa 4015/1.

BACKGROUND OF THE INVENTION

The present Invention relates to a new and distinct cultivar of *Sanvitalia* plant, botanically known as *Sanvitalia procumbens* and hereinafter referred to by the name 'QuHa 4015/1'.

The new *Sanvitalia* was discovered by the Inventor in 1999 as a naturally-occurring branch mutation of an unnamed proprietary *Sanvitalia procumbens* seedling selection, not patented, in a greenhouse in Venhuizen, The Netherlands. The new *Sanvitalia* was selected by the Inventor on the basis of its larger inflorescence size.

Asexual reproduction of the new *Sanvitalia* by vegetative cuttings was first conducted in Venhuizen, The Netherlands in 1999. Asexual reproduction by vegetative cuttings has shown that the unique features of this new *Sanvitalia* are stable and reproduced true to type in successive generations.

SUMMARY OF THE INVENTION

The cultivar 'QuHa 4015/1' has not been observed under all possible environmental conditions. The phenotype may vary somewhat with variations in environment such as temperature and light level without, however, any variance in genotype.

The following traits have been repeatedly observed and are determined to be the unique characteristics of 'QuHa 4015/1'. These characteristics in combination distinguish 'QuHa 4015/1' as a new and distinct *Sanvitalia*:

1. Low mounding and spreading plant habit.
2. Dark green-colored foliage.
3. Early and freely flowering habit.
4. Bright yellow-colored ray florets.

Compared to plants of the parent selection, plants of the new *Sanvitalia* are faster growing, have darker green-colored leaves, are more freely flowering and have larger inflorescences.

Plants of the new *Sanvitalia* can be compared to plants of the *Sanvitalia* cultivar Aztekengold, not patented. In side-by-side comparisons conducted in Venhuizen, The Netherlands, plants of the new *Sanvitalia* differed from plants of the cultivar Aztekengold in the following characteristics:

1. Plants of the new *Sanvitalia* grew faster than plants of the cultivar Aztekengold.
2. Plants of the new *Sanvitalia* had larger inflorescences than plants of the cultivar Aztekengold.
3. Ray florets of plants of the new *Sanvitalia* were darker yellow in color than ray florets of plants of the cultivar Aztekengold.

BRIEF DESCRIPTION OF THE PHOTOGRAPHS

The accompanying colored photographs illustrate the overall appearance of the new *Sanvitalia* showing the colors as true as it is reasonably possible to obtain in colored reproductions of this type. Colors in the photographs may differ from the color values cited in the detailed botanical description which accurately describe the colors of the new *Sanvitalia*.

The photograph at the top of the sheet comprises a side perspective view of a typical flowering plant of 'QuHa 4015/1' grown in a container.

The photograph at the bottom of the sheet comprises a close-up view of typical inflorescence buds, typical open inflorescences, and the upper and lower surfaces of typical leaves of 'QuHa 4015/1'.

DETAILED BOTANICAL DESCRIPTION

The aforementioned photographs and following observations and measurements describe plants grown in Lompoc, Calif., under commercial practice during the summer and autumn in a polycarbonate-covered greenhouse with day temperatures ranging from 21 to 27° C., night temperatures ranging from 16 to 18° C., and light levels ranging from 4,000 to 9,000 foot-candles. Plants used for the photographs and botanical description were grown in 20-cm containers and grown for about 14 weeks.

In the following description, color references are made to The Royal Horticultural Society Colour Chart, 1995 Edition, except where general terms of ordinary dictionary significance are used.

Botanical classification: *Sanvitalia procumbens* cultivar QuHa 4015/1.

Parentage: Naturally-occurring branch mutation of an unnamed proprietary seedling selection of *Sanvitalia procumbens*, not patented.

Propagation:

*Type.*—Vegetative cuttings.

*Time to initiate roots, summer and winter.*—About 6 days at 22° C.

*Time to produce a rooted young plant.*—Summer: About 10 days at 22° C. Winter: About 15 days at 22° C.

*Root description.*—Fine; white in color.

Plant description:

*Appearance.*—Low mounding and spreading plant habit. Freely branching with about 10 basal branches per plant and lateral branches forming potentially every node; indeterminate growth habit; moderately vigorous.

*Plant height.*—About 18 cm.

*Plant width.*—About 46 cm.

*Lateral branches.*—Length: About 42 cm. Diameter: About 2.5 mm. Internode length: About 7.5 cm. Strength: Moderately strong. Orientation: Horizontally creeping; curling. Texture: Sparsely pubescent. Color: 146A overlain with close to 187A. Fully opened, upper surface: 14A; color does not fade with subsequent development. Fully opened, lower surface: 145A.

*Disc florets.*—Quantity/arrangement: More than 100 disc florets per inflorescence massed at center of receptacle. Length: About 2 mm. Width: At apex, about 1 mm; at base, less than 1 mm. Shape: Tubular; minute. Apex: Five-pointed. Color: 144A. Color, mature: Apex: 154A. Mid-section and base: 144A.

*Phyllaries.*—Quantity/arrangement: About five in a single whorl. Length: About 5 mm. Width: About 4 mm. Shape: Elliptic. Apex: Acute. Depth (height): About 6 mm. Diameter of disc: About 5.5 mm. Receptacle diameter: About 1 cm. Receptacle height: About 4 mm.

*Ray florets.*—Quantity/arrangement: About 13 ray florets per inflorescence arranged in a single whorl. Orientation: Initially upright, then about 90° from vertical and reflexing with subsequent development. Length: About 1 cm. Width: About 2.5 mm. Shape: Ligulate. Apex: Rounded to slightly emarginate. Base: Acute. Margin: Entire. Texture, upper and lower surfaces: Smooth, glabrous. Color: When opening, upper surface: 14B. When opening, lower surface: 145A to 145B.

Inflorescence description:

*Appearance.*—Daisy-type inflorescence form with ligulate-shaped ray florets. Solitary inflorescences borne on terminals above foliage. Disk and ray florets develop acropetally on a capitulum. Inflorescences persistent. Inflorescences not fragrant.

*Quantity.*—Freely flowering; typically one terminal inflorescence per lateral branch; during the flowering period, more than 400 inflorescences and buds will develop per plant.

*Flowering response.*—Early flowering, plants begin to flower about four weeks after planting unrooted cuttings. Plants flower continuously during the summer in the garden.

*Inflorescence longevity.*—Inflorescences maintain good color and substance for about one week on the plant.

*Inflorescence bud.*—Height: About 4 mm. Diameter: About 6 mm. Shape: Oblate. Color: 144B to 144C.

*Inflorescence size.*—Diameter: About 2 cm.

*Foliage description.*—Arrangement: Opposite, simple. Length: About 3 cm. Width: About 1.2 cm. Shape: Elliptic to slightly deltoid. Apex: Broadly acute. Base: Clasping; sessile. Margin: Entire. Texture: Upper surface: Sparsely pubescent. Lower surface: Glabrous. Venation pattern: Pinnate. Color: Young foliage, upper surface: 147A. Young foliage, lower surface: 138A. Mature foliage, upper surface: 147A. Mature foliage, lower surface: 147B. Venation, upper surface: 145C. Venation, lower surface: 145C to 145D. Base: Truncate. Margin: Entire. Texture, upper and lower surfaces: Slightly coarse. Color, upper and lower surfaces: 138A.

*Peduncles.*—Length: About 2.5 cm. Diameter: About 1 mm. Strength: Moderately strong. Aspect: Upright or outward on horizontal lateral branches. Texture: Slightly pubescent. Color: 146B overlain with close to 187A.

*Reproductive organs.*—Androecium: Present on disc florets only. Stamen quantity: Five per floret. Anther length: Less than 1 mm. Anther shape: Oblong. Anther color: 151C. Pollen amount: Scarce. Pollen color: 151C. Gynoecium: Present on both ray and disc florets. Pistil quantity: One per floret. Pistil length: About 2 mm. Stigma shape: Bi-parted. Stigma color: 12A. Style length: About 1 mm. Style color: 12A. Ovary color: 145D.

*Fruit/seed.*—Fruit and seed production has not been observed.

Disease/pest resistance: Resistance to pathogens and pests common to *Sanvitalias* has not been observed on plants grown under commercial greenhouse conditions.

Weather tolerance: Plants of the new *Sanvitalia* have been observed to have good garden performance and have been observed to be tolerant to rain and wind and temperatures from 2 to 40° C.

It is claimed:

1. A new and distinct cultivar of *Sanvitalia* plant named 'QuHa 4015/1', as illustrated and described.

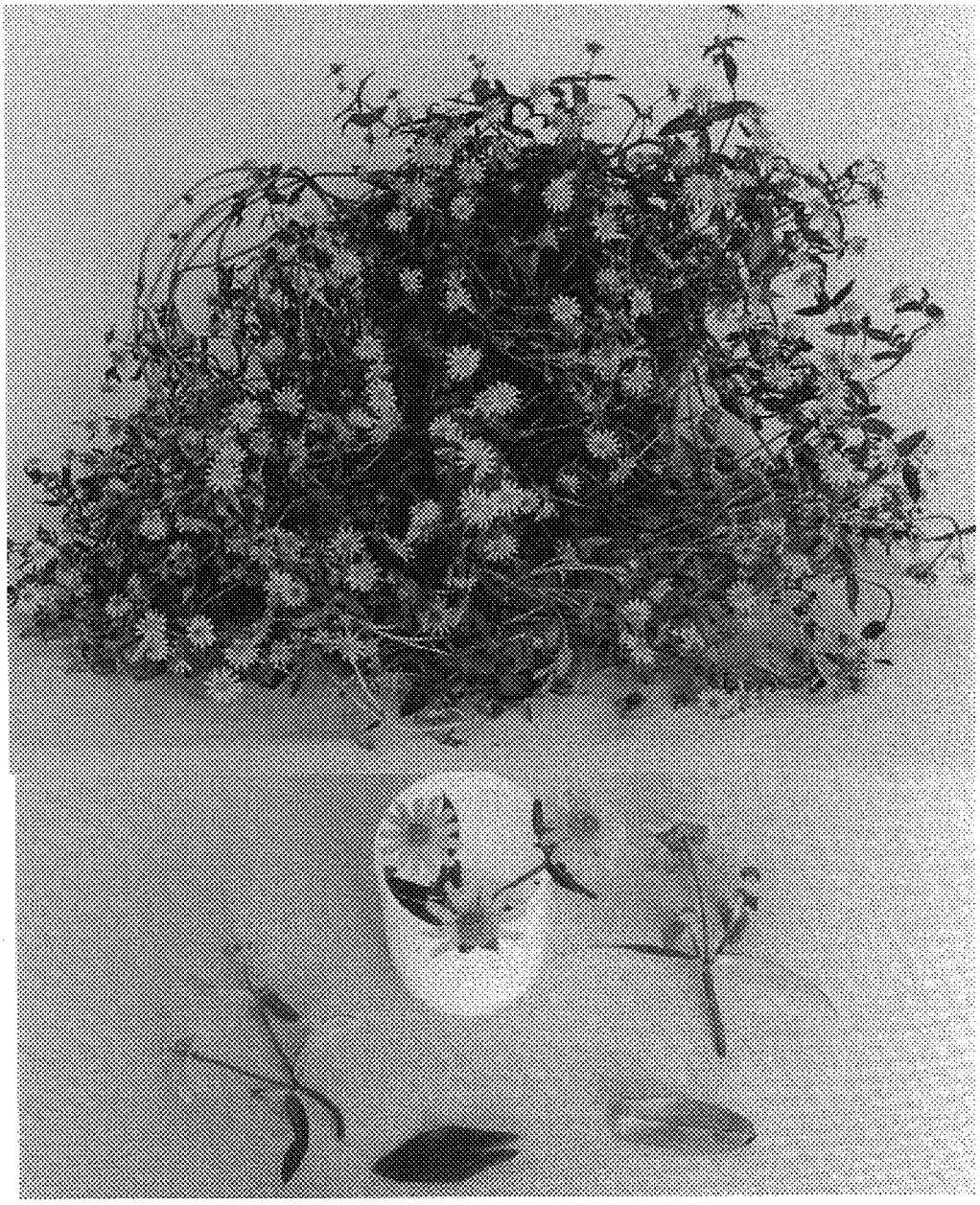

* * * * *